United States Patent
Baughman et al.

(10) Patent No.: US 10,180,688 B2
(45) Date of Patent: Jan. 15, 2019

(54) OPTIMIZATION THROUGH USE OF CONDUCTIVE THREADS AND BIOMETRIC DATA

(71) Applicant: International Business Machines Corporation, Armonk, NY (US)

(72) Inventors: Aaron K. Baughman, Silver Spring, MD (US); Arun Joseph, Bangalore (IN); Brian M. O'Connell, Cary, NC (US); Diwesh Pandey, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 259 days.

(21) Appl. No.: 15/180,619

(22) Filed: Jun. 13, 2016

(65) Prior Publication Data

US 2017/0357274 A1 Dec. 14, 2017

(51) Int. Cl.
| | |
|---|---|
| *G05D 5/06* | (2006.01) |
| *G06N 3/04* | (2006.01) |
| *A61B 5/00* | (2006.01) |
| *A61B 5/0205* | (2006.01) |
| *A61B 5/107* | (2006.01) |
| *G06F 19/00* | (2018.01) |
| *G16H 40/67* | (2018.01) |
| *A41D 15/00* | (2006.01) |
| *A41D 1/00* | (2018.01) |
| *H01G 9/20* | (2006.01) |

(Continued)

(52) U.S. Cl.
CPC ............. *G05D 5/06* (2013.01); *A61B 5/0022* (2013.01); *A61B 5/0205* (2013.01); *A61B 5/1072* (2013.01); *A61B 5/6804* (2013.01); *G06F 19/00* (2013.01); *G06N 3/0445* (2013.01); *G16H 40/67* (2018.01); *A41D 1/005* (2013.01); *A61B 5/01* (2013.01); *A61B 5/0533* (2013.01); *A61B 5/0537* (2013.01); *A61B 5/6898* (2013.01); *H01G 9/20* (2013.01)

(58) Field of Classification Search
CPC ..................... G06F 2217/32; G06F 17/30259; A41D 15/00
USPC ............................ 700/141, 303; 2/221, 237
See application file for complete search history.

(56) References Cited

U.S. PATENT DOCUMENTS

| | | |
|---|---|---|
| 4,598,376 A | 7/1986 | Burton et al. |
| 5,495,568 A | 2/1996 | Beavin |
| 6,324,437 B1 | 11/2001 | Frankel et al. |

(Continued)

FOREIGN PATENT DOCUMENTS

WO  2014149199 A1  9/2014

OTHER PUBLICATIONS

Orsini, L. "Soft Electronics Makes Wearable Computing Something You'd Actually Wear", retrieved from http://readwrite.com/2014/03/11/wearable-computing-soft-electronics-clothing/; Mar. 2014.

(Continued)

*Primary Examiner* — Michael J Brown
(74) *Attorney, Agent, or Firm* — Brown & Michaels, PC; James Nock (57) ABSTRACT

In a method, a computer receives biometric data from sensors. The computer compares the biometric data to predefined levels of biometric data. The computer determines a score based on the biometric data. The computer compares the score to previously stored scores. The computer sends a score to conductive threads if the score is not acceptable.

20 Claims, 4 Drawing Sheets

(51) Int. Cl.
  *A61B 5/01* (2006.01)
  *A61B 5/053* (2006.01)

(56) References Cited

U.S. PATENT DOCUMENTS

| | | | | |
|---|---|---|---|---|
| 7,992,217 | B2* | 8/2011 | Hyde | A61B 5/1077 2/1 |
| 2014/0244361 | A1 | 8/2014 | Zhang et al. | |
| 2014/0280610 | A1 | 9/2014 | Chen et al. | |
| 2015/0370320 | A1* | 12/2015 | Connor | A61B 5/6831 345/173 |
| 2016/0350819 | A1* | 12/2016 | Mitchell | G06Q 30/0621 |

OTHER PUBLICATIONS

Stoppa et al. "Wearable Electronics and Smart Textiles: A Critical Review", Center for Space Human Robotics; Sensors Jul. 2014.
Cho, G. "Smart Clothing Technology and Applications", CRC Press, Taylor & Francis Group, 2010.
Salvado et al. "Textile Materials for the Design of Wearable Antennas: A Survey", Sensors; Nov. 2012.
"A Beginner's Guide to Recurrent Networks and LSTMs" retrieved from http://deeplearning4j.org/lstm.html; as early as Sep. 2015.
"Smart Textiles Products Page", retrieved from http://www.proetex.org/final%20proetex%20learning/Functions.htm, as early as Apr. 2009.
Coxworth, B. "Squid-inspired tech could lead to color-changing smart materials, retrieved from http://www.gizmag.com/squid-inspired-color-changing-clothes/22383/, May 2012."
Alleyne, A. "When chemistry meets couture: Clothes that change color with the climate" http://edition.cnn.com/2015/02/10/world/when-chemistry-meets-couture/, at least as early as Jun. 29, 2015.
Williams, A. "Karma Chameleon: Smart Clothes that change their shape and colour as you move . . . and can even charge your phone" http://www.dailymail.co.uk/sciencetech/article-2311181/Karma-chameleon-Smart-clothes-change-shape-colour-move.html#ixzz46Wvvt0LB; Apr. 2013.

* cited by examiner

OPTIMIZATION THROUGH USE OF CONDUCTIVE THREADS AND BIOMETRIC DATA

BACKGROUND

The present invention relates to garment optimization, and more specifically to altering a garment while being worn by a user, based on biometric data.

Garment comfort for a user can vary over time while the garment is being worn. It can be difficult for a user to change or alter the garment to increase comfort level.

SUMMARY

According to one embodiment of the present invention, a method of optimizing a garment being worn by a user is disclosed. The garment includes a plurality of conductive threads forming a fabric, with the fabric comprising a plurality of sensors. The method comprising the steps of: a computer receiving biometric data from the sensors in the garment; the computer comparing the biometric data received from the sensors to predefined levels of biometric data associated with the user; the computer determining a comfort score of the garment for the user based on the biometric data; the computer comparing the comfort score of the garment to previously stored comfort scores; and if the comfort score is not acceptable for the garment currently being worn by the user, the computer sending a signal to the conductive threads of the garment while being worn by the user to alter a feature of the garment selected from the group consisting of: texture, shape and size.

According to another embodiment of the present invention, a computer program product for optimizing a garment being worn by a user is disclosed. The garment includes: a plurality of conductive threads forming a fabric, with the fabric comprising a plurality of sensors. A computer comprising at least one processor, one or more memories, one or more computer readable storage media, executes the computer program product comprising a computer readable storage medium having program instructions embodied therewith. The program instructions executable by the computer to perform a method comprising: receiving, by the computer, biometric data from the sensors in the garment; comparing, by the computer, the biometric data received from the sensors to predefined levels of biometric data associated with the user; determining, by the computer, a comfort score of the garment for the user based on the biometric data; comparing, by the computer, the comfort score of the garment to previously stored comfort scores; and if the comfort score is not acceptable for the garment currently being worn by the user, sending, by the computer, a signal to the conductive threads of the garment while being worn by the user to alter a feature of the garment selected from the group consisting of: texture, shape and size.

According to another embodiment of the present invention, a computer system for optimizing a garment being worn by a user is disclosed. The garment includes: a plurality of conductive threads forming a fabric, with the fabric comprising a plurality of sensors. The computer system comprising a computer comprising at least one processor, one or more memories, one or more computer readable storage media having program instructions executable by the computer to perform the program instructions comprising: receiving, by the computer, biometric data from the sensors in the garment; comparing, by the computer, the biometric data received from the sensors to predefined levels of biometric data associated with the user; determining, by the computer, a comfort score of the garment for the user based on the biometric data; comparing, by the computer, the comfort score of the garment to previously stored comfort scores; and if the comfort score is not acceptable for the garment currently being worn by the user, sending, by the computer, a signal to the conductive threads of the garment while being worn by the user to alter a feature of the garment selected from the group consisting of: texture, shape and size.

DETAILED DESCRIPTION

In an illustrative embodiment of the present invention, the garment being worn is comprised of a fabric that features electronics and interconnections woven into the garment, such as conductive threads, allowing for physical flexibility. Most threads are metalized with an alloy of various metals, which can include silver, copper, tin and nickel. The conductive threads can receive an electric signal which can induce the conductive threads to alter the density of the threads at one given place of the garment while being worn by the user. The conductive threads are made of shape memory materials (SMM). The material changes their shape according to stimuli, such as heat of an electric current. The SMM are shape memory alloys (SMA) and shape memory polymers (SMP). An example of SMA is nickel titanium and copper based alloy.

Also present within or embedded into the fabric is a plurality of small sensors. The sensors embedded within the fabric monitor biometrics of the user. For example, behavioral characteristics related to the pattern of behavior of a person, including but not limited to gait, and voice and physiological changes of the user such as heat, moisture, respiration, salinity, body temperature, heart rate, and other changes. Additional sensors may provide data regarding the user. An additional sensor may be a mobile device which may be, but is not limited to, a smart phone, smart watch, heart monitor, activity tracker or other devices. The mobile device may include a heart rate monitor, camera, microphone, body temperature sensor, or sensors for other biometric data. The additional sensors may be connected to and receive input from the sensors embedded within the fabric of the garment being worn by the user. Alternatively, the additional sensors may be in communication with a garment optimization program.

In an illustrative embodiment, it is recognized that the methods, computer program products and computer systems may be implemented through a garment of a user which collects information from embedded sensors and alters the shape of the garment through the conductive threads. The shape of the garment is controlled using a sensor, such as a control sensor, which triggers electric current in the conductive threads to change the shape of the garment. The conductive threads are preferably made of SMA.

The garment is connected to a server computer in connection with a storage device or repository. The server may also be connected to a mobile device which provides additional input to the garment optimization program on the server computer. Input from the garment optimization program may be received by a processor connected to the conductive threads of the garment. The garment is preferably worn next to bare skin of the user.

Figure 1:
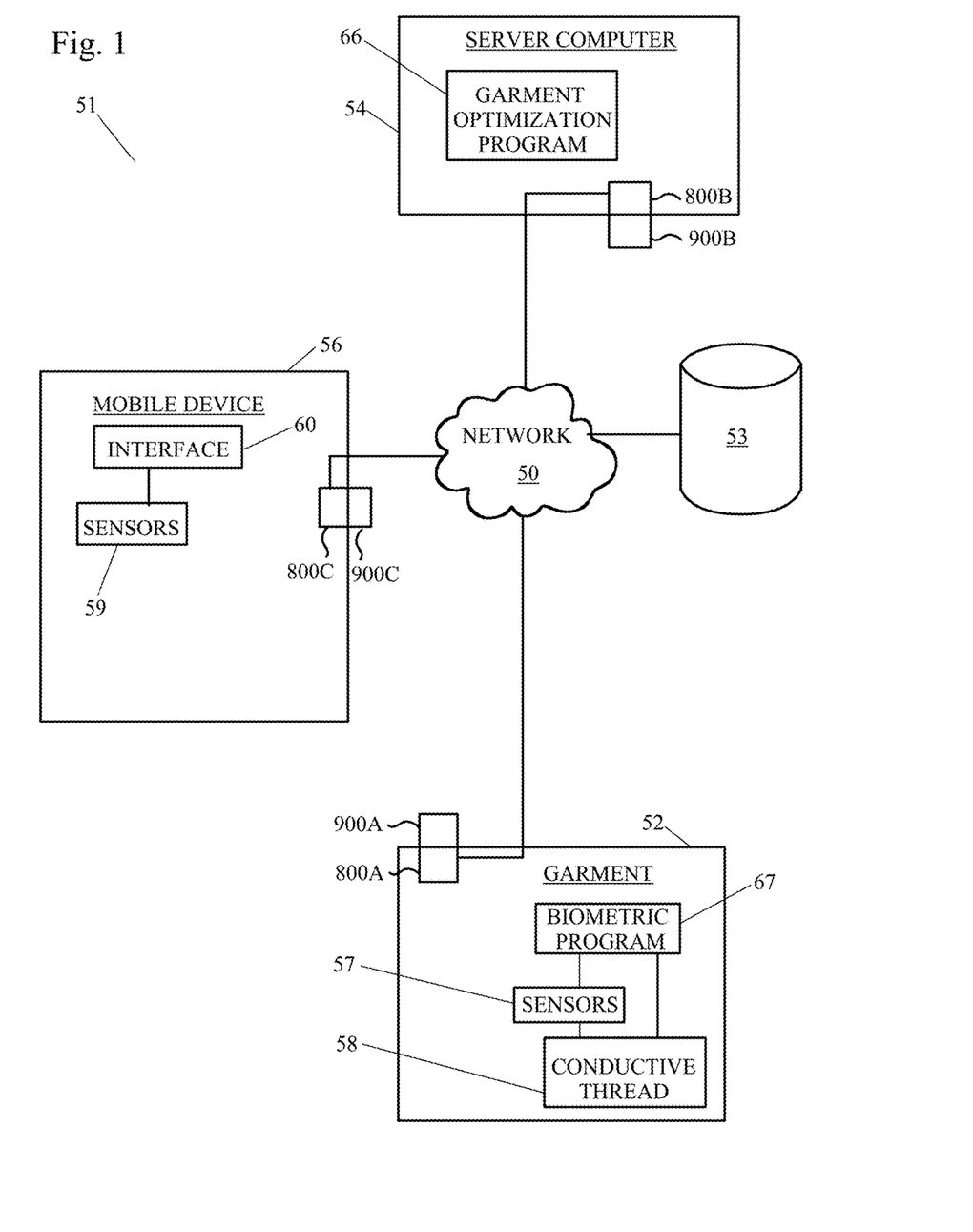
FIG. 1 depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wire, wireless communication links, or fiber optic cables.

In the depicted example, a garment 52, a mobile device 56, a repository 53, and a server computer 54 connect to network 50. In other exemplary embodiments, network data processing system 51 may include additional client or device computers, storage devices or repositories, server computers, and other devices not shown.

Figure 4:
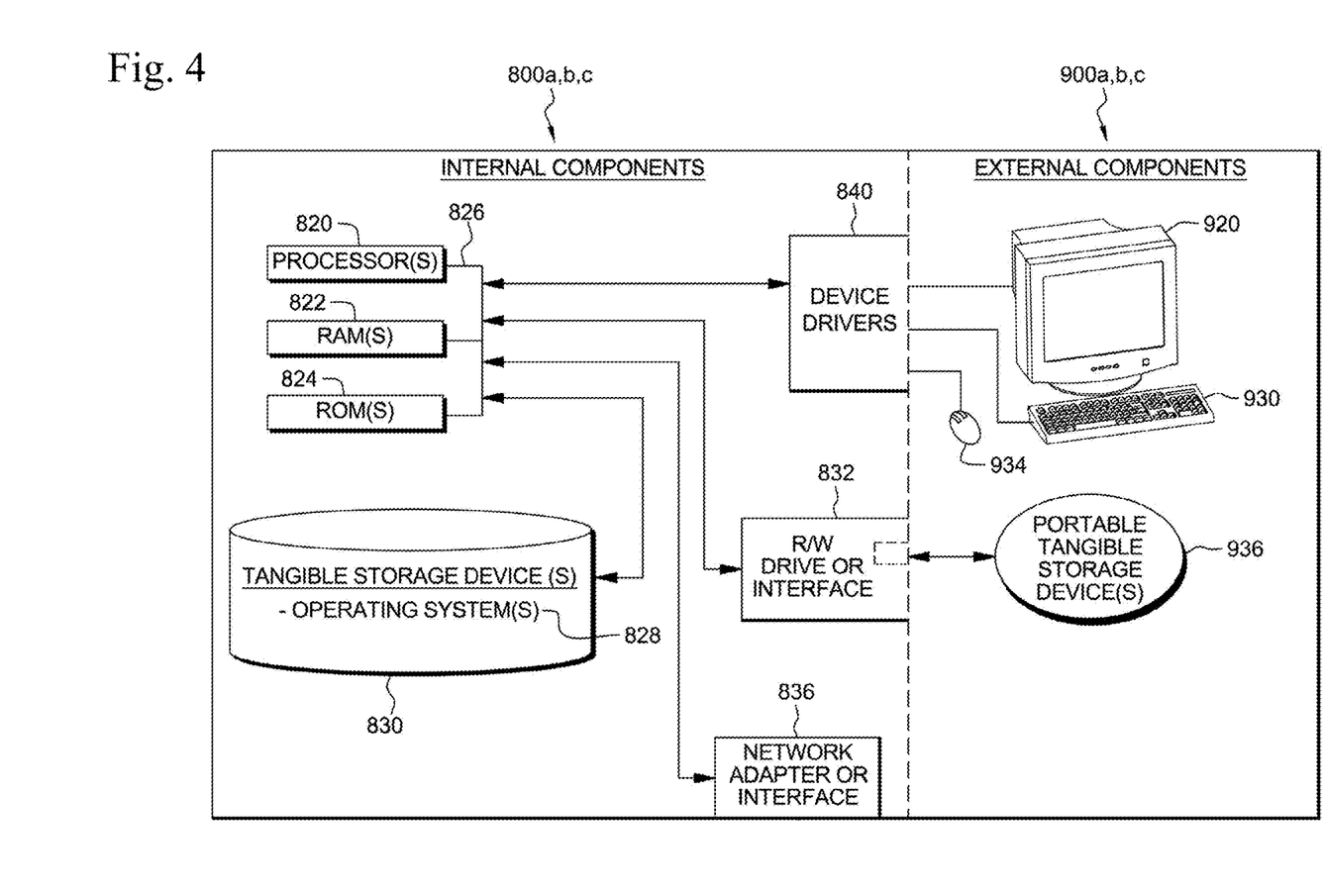
FIG. 4 illustrates internal and external components of a client computer and a server computer in which illustrative embodiments may be implemented.

Garment 52 includes a set of internal components 800a and a set of external components 900a, further illustrated in FIG. 4. Garment 52 may be, for example a garment with conductive threads 58 and embedded sensors 57. One or more of the embedded sensors may contain a processor. The embedded sensors are capable of outputting sensed data. The sensors 57 and conductive threads 58 maybe in communication with a biometric program 67.

Mobile device 56 includes a set of internal components 800c and a set of external components 900c illustrated in FIG. 4. Mobile device 56 may be, for example, a cell phone, a personal digital assistant, a smart phone, smart watch, heart monitor, activity tracker and other devices. The mobile device 56 may contain an interface 60 and sensors 59. The interface 60 may accept commands and data entry from a user, such as input to regarding comfort levels based on biometrics of the user as well as sensor data form sensors 59 or embedded sensors 57. For example, behavioral characteristics related to the pattern of behavior of a person, including but not limited to gait, and voice and physiological changes of the user such as heat, moisture, salinity, body temperature, heart rate, and other changes. The interface can be, for example, a command line interface, a graphical user interface (GUI), or a web user interface (WUI). While not shown, the biometric program 67 and/or the garment optimization program may be present on the mobile device 56.

Server computer 54 includes a set of internal components 800b and a set of external components 900b illustrated in FIG. 4. Server computer 54 may contain an interface. The interface can be, for example, a command line interface, a graphical user interface (GUI), or a web user interface (WUI) to access a garment optimization program 66 and receive input from sensors 57 within the garment or sensors 59 of the mobile device.

In the depicted example, server computer 54 provides information, such as boot files, operating system images, and applications to mobile device 52 and/or garment 52. Server computer 54 can compute the information locally or extract the information from other computers on network 50.

Program code and programs such as garment optimization program 66 and biometric program 67 may be stored on at least one of one or more computer-readable tangible storage devices 830 shown in FIG. 4, on at least one of one or more portable computer-readable tangible storage devices 936 as shown in FIG. 4, or on storage unit 53 connected to network 50, or may be downloaded to a computer, such as mobile device 56 or garment 52 or server computer 54, for use. For example, program code and programs such as garment optimization program 66 and biometric program 67 may be stored on at least one of one or more storage devices 830 on server computer 54 and downloaded to mobile device 56 or garment 52 over network 50 for use with the garment 52. Alternatively, server computer 54 can be a web server, and the program code, and programs such as garment optimization program 66 or biometric program 67 may be stored on at least one of the one or more storage devices 830 on server computer 54 and accessed on mobile device 56 or garment 52. In other exemplary embodiments, the program code, and programs such as garment optimization program 66 or biometric program 67 may be stored on at least one of one or more computer-readable storage devices 830 on mobile device 56 or to garment 52 or distributed between two or more servers.

In the depicted example, network data processing system 51 is the Internet with network 50 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 51 also may be implemented as a number of different types of networks, such as, for example, an intranet, local area network (LAN), or a wide area network (WAN). FIG. 1 is intended as an example, and not as an architectural limitation, for the different illustrative embodiments.

Figure 2:
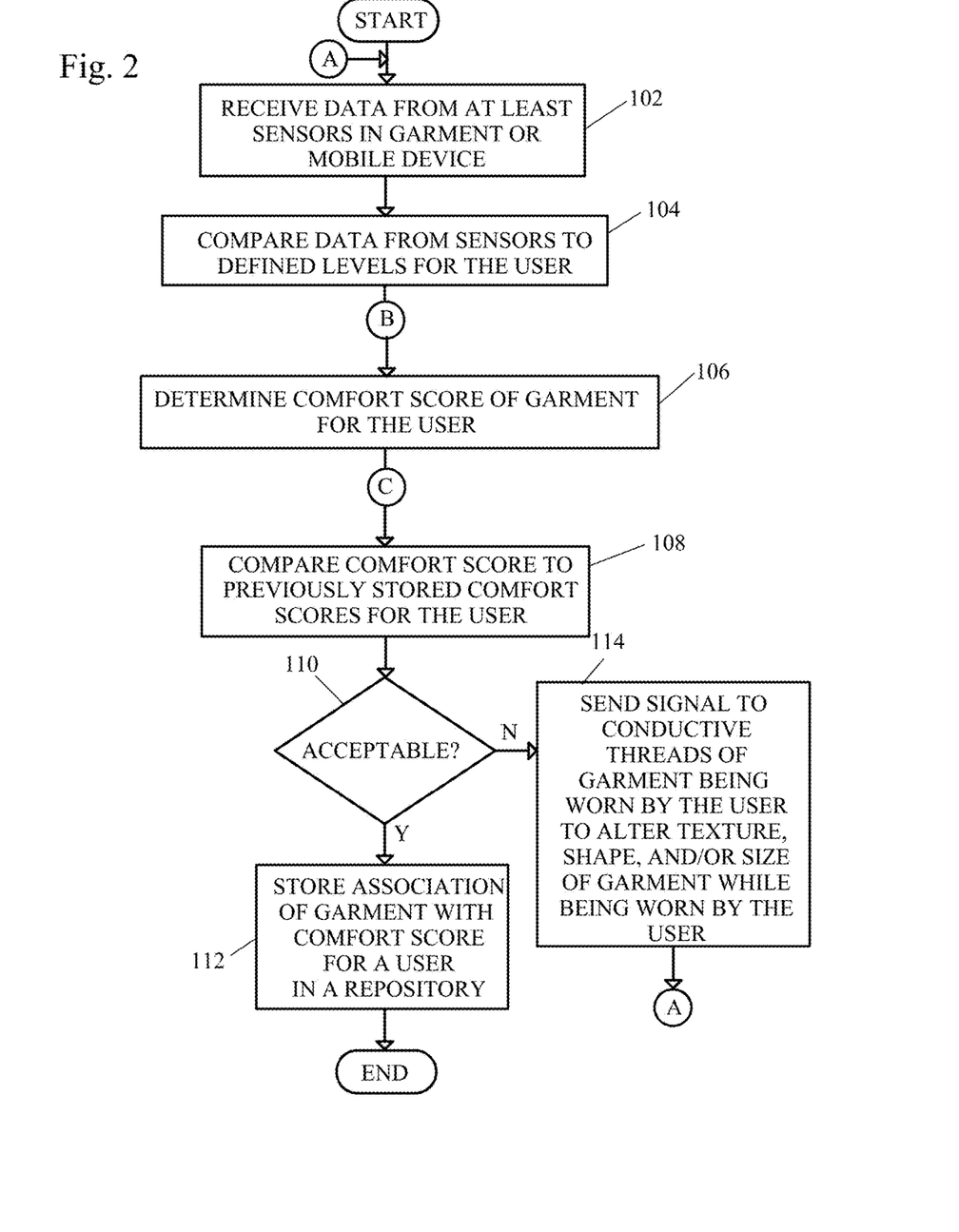
FIG. 2 shows a flow diagram of a method of garment optimization.

FIG. 2 shows a method of garment optimization.

In a first step, a garment optimization program 66 receives data from sensors 57 in the garment 52 (step 102). Data may also be received from the sensors 59 of the mobile device 52.

The garment optimization program 66 compares the data received from sensors 57, 59 to defined levels for the user (step 104). The defined levels may be stored in repository 53. The defined levels may be set by the user or predetermined.

The garment optimization program 66 determines a comfort score of the garment for the user, based on the defined levels (step 106).

Figure 3:
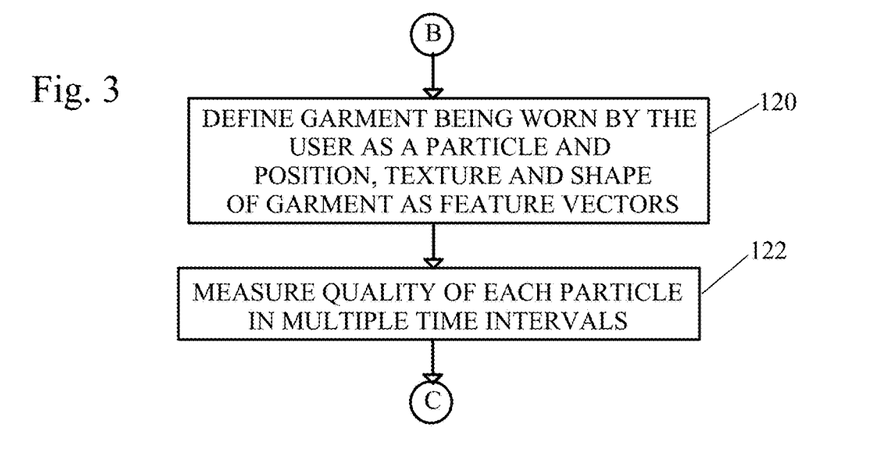
FIG. 3 shows a flow diagram of a method of determining comfort of a garment being worn by the user.

FIG. 3 shows a flow diagram of a method of determining a comfort score of a garment being worn by the user (step 106). The comfort score of the garment may be determined using a recurrent neural network (RNN).

A RNN is a class of artificial neural network where connections between units form a directed cycle. This creates an internal state of the network which allows it to exhibit dynamic temporal behavior. The RNNs can use an internal memory to process arbitrary sequences of inputs and allows unsegmented movements or biometric data to determine comfort level of a user as it relates garment being worn.

In one embodiment, a deep learning RNN, such as a long short term memory (LSTM) network is used. LSTMs help preserve error and uses memory weights to recall previous states and can change combined values that enter an activation function.

By maintaining a more constant error, recurrent nets are allowed to continue to learn over many time steps (over 1000), thereby opening a channel to link causes and effects remotely.

LSTMs contain information outside the normal flow of the recurrent network in a gated cell. Information can be stored in, written to, or read from a cell, much like data in a computer's memory. The cell makes decisions in regards to what is stored, and when to allow reads, writes and erasures, via gates that open and close. The gates act on the signals they receive, and similar to a neural network's nodes, in that information is blocked or passed based on its strength and import, which is filtered by sets of weights. Those weights, like the weights that modulate input and hidden states, are adjusted via a recurrent networks learning process. That is, the cells learn when to allow data to enter, leave or be deleted through the iterative process of making guesses, back-propagating error, and adjusting weights via gradient descent. The gates are analog and are implemented with element-wise multiplication by sigmoids, which are all in the range of 0-1. The input provided to the cells is acquired from the sensors in the garment. The output of the LSTM is a measure of how well the garment suits the current environment or fits the user.

Using the LSTM RNN, the garment optimization program 66 defines the garment being worn by the user, with each garment being worn being defined as a particle and features of the garment being defined as feature vectors (step 120). The dimensionality of the feature vectors will be the same for each garment being tracked. The feature vectors may include, but is not limited to position, texture and shape of the garment.

The garment optimization program 66 measures a quality of each particle in multiple intervals of time (step 122). The measurement of the quality is accomplished through the LSTM. The LSTM accepts feature vectors from the particle representing a garment. The vectors are normalized and input into the LSTM. Sigmoid functions are applied to the convergence of the feature vector values. Memory weights are then applied. The memory weights are updated to remember the state of the particle for a time interval. The output of the LSTM measure the comfort of the garment relative to the user.

Referring back to FIG. 2, the garment optimization program 66 compares the determined comfort score to previously stored comfort scores for the user or alternatively, if a previously stored comfort score is not present for the user, to a predetermined comfort score for the garment being worn by the user (step 108).

If the comfort score is acceptable (step 110), the association of the garment with the comfort score for a user is stored in a repository (step 112), for example repository 53. The comfort score is determined to be acceptable based on how close the individual's social score is to global score and a neighbor social score. Each particle (garment) tries to come in equilibrium state, which is to come closer to the "nbest" or "gbest" value. An "nbest" value will be always less the or equal to "gbest" value. Therefore, the particle (garment) will first try to move towards an "nbest" value. The optimum score will be reached when there is no further movement in the particles. It should be noted that a runtime limit for the optimization of particle to get the best value or optimum value. Furthermore, there may be a time limit or timer associated with how often the garment can change.

If the comfort score is not acceptable (step 110), the garment optimization program alters the electrical signals being sent to the conductive threads of the garment to alter the texture, shape and/or size while the garment is being worn by the user (step 114) and the method returns to step 102. For example, a signal may be sent to the conductive threads to alter the density of the threads and thus the shape and/or texture of the garment while being worn by the user. A different signal may be used to control the shape, texture and color of the garment or multiple garments. The shape of the garment may be controlled by an intensity of electrical signals.

FIG. 4 illustrates internal and external components of a garment 52, a mobile device 56, and server computer 54 in which illustrative embodiments may be implemented. In FIG. 4, a garment 52, server computer 54, and a mobile device 56 may include respective sets of internal components 800a, 800b, 800c and external components 900a, 900b, 900c. Each of the sets of internal components 800a, 800b, 800c includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, garment optimization program 66, and biometric program 67 are stored on one or more of the computer-readable tangible storage devices 830 for execution by one or more of the processors 820 via one or more of the RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b, 800c also includes a R/W drive or interface 832 to read from and write to one or more portable computer-readable tangible storage devices 936 such as a CD-ROM, DVD, memory stick, magnetic tape, magnetic disk, optical disk or semiconductor storage device. Garment optimization program 66 and biometric program 67 can be stored on one or more of the portable computer-readable tangible storage devices 936, read via R/W drive or interface 832 and loaded into hard drive 830.

Each set of internal components 800a, 800b, 800c also includes a network adapter or interface 836 such as a TCP/IP adapter card. Garment optimization program 66 and biometric program 67 can be downloaded to the personal imaging device 52 and server computer 54 from an external computer via a network (for example, the Internet, a local area network or other, wide area network) and network adapter or interface 836. From the network adapter or interface 836, power management program 66 and sensor data capture program 67 is loaded into hard drive 830. Garment optimization program 66 and biometric program 67 can be downloaded to the mobile device 56 and server computer 54 from an external computer via a network (for example, the Internet, a local area network or other, wide area network) and network adapter or interface 836. From the network adapter or interface 836, Garment optimization program 66 and biometric program 67 are loaded into hard drive 830. The network may comprise copper wires, optical fibers, wireless transmission, routers, firewalls, switches, gateway computers and/or edge servers.

Each of the sets of external components 900a, 900b, 900c includes a computer display monitor 920, a keyboard 930, and a computer mouse 934. Each of the sets of internal components 800a, 800b, 800c also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Garment optimization program 66 and biometric program 67 can be written in various programming languages including low-level, high-level, object-oriented or non object-oriented languages. Alternatively, the functions of a garment optimization program 66 and biometric program 67 can be implemented in whole or in part by computer circuits and other hardware (not shown).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of optimizing a garment being worn by a user, the garment comprising: a plurality of conductive threads forming a fabric, the fabric comprising a plurality of sensors, the method comprising the steps of:
   a computer receiving biometric data from the sensors in the garment;
   the computer comparing the biometric data received from the sensors to predefined levels of biometric data associated with the user;
   the computer determining a comfort score of the garment for the user based on the biometric data, the determining further comprising:
      a long short term memory network in communication with the computer receiving a particle defined as the garment being worn by the user and at least one feature of the garment as feature vectors of the garment;
      the long short term memory network measuring a quality of each particle in multiple intervals of time by: normalizing feature vectors; converging the feature vectors; applying sigmoid functions to the convergence of the feature vectors; applying memory weights to the convergence of the feature vectors; updating the memory weights to store a state of the particle at an interval of time; and outputting a measure of comfort of the garment relative to the user as a comfort score to the computer;
   the computer comparing the comfort score of the garment to previously stored comfort scores; and
   if the comfort score is not acceptable for the garment currently being worn by the user, the computer sending a signal to the conductive threads of the garment while being worn by the user to alter a feature of the garment selected from the group consisting of: texture, shape and size.

2. The method of claim 1, wherein, if the comfort score is acceptable, storing the comfort score of the garment associated with the user in a repository.

3. The method of claim 1, wherein the garment is worn next to the skin of the user.

4. The method of claim 1, further comprising the step of receiving biometric data of the user from a mobile device.

5. The method of claim 1, wherein the conductive threads are made of shape memory materials and alter the shape based on stimuli.

6. The method of claim 5, wherein the shape memory materials are selected from the group consisting of: shape memory alloys and shape memory polymers.

7. The method of claim 1, wherein the long short term memory network comprises the computer.

8. A computer program product for optimizing a garment being worn by a user, the garment comprising: a plurality of conductive threads forming a fabric, the fabric comprising a plurality of sensors, a computer comprising at least one processor, one or more memories, one or more computer readable storage media, the computer program product comprising a computer readable storage medium having program instructions embodied therewith, the program instructions executable by the computer to perform a method comprising:
   receiving, by the computer, biometric data from the sensors in the garment;
   comparing, by the computer, the biometric data received from the sensors to predefined levels of biometric data associated with the user;
   determining, by the computer, a comfort score of the garment for the user based on the biometric data, the determining further comprising:
      receiving, by a long short term memory network in communication with the computer, a particle defined as the garment being worn by the user and at least one feature of the garment as feature vectors of the garment;
      measuring, by the long short term memory network, a quality of each particle in multiple intervals of time by: normalizing feature vectors; converging the feature vectors; applying sigmoid functions to the convergence of the feature vectors; applying memory weights to the convergence of the feature vectors; updating the memory weights to store a state of the particle at an interval of time; and outputting a measure of comfort of the garment relative to the user as a comfort score to the computer;
   comparing, by the computer, the comfort score of the garment to previously stored comfort scores; and
   if the comfort score is not acceptable for the garment currently being worn by the user, sending, by the computer, a signal to the conductive threads of the garment while being worn by the user to alter a feature of the garment selected from the group consisting of: texture, shape and size.

9. The computer program product of claim 8, wherein, if the comfort score is acceptable, storing the comfort score of the garment associated with the user in a repository.

10. The computer program product of claim 8, wherein the garment is worn next to the skin of the user.

11. The computer program product of claim 8, further comprising the program instructions of receiving, by the computer, the biometric data of the user from a mobile device.

12. The computer program product of claim 8, wherein the conductive threads are made of shape memory materials and alter the shape based on stimuli.

13. The computer program product of claim 12, wherein the shape memory materials are selected from the group consisting of: shape memory alloys and shape memory polymers.

14. The computer program product of claim 8, wherein the long short term memory network comprises the computer.

15. A computer system for optimizing a garment being worn by a user, the garment comprising: a plurality of conductive threads forming a fabric, the fabric comprising a plurality of sensors, the computer system comprising a computer comprising at least one processor, one or more memories, one or more computer readable storage media having program instructions executable by the computer to perform the program instructions comprising:
   receiving, by the computer, biometric data from the sensors in the garment;

comparing, by the computer, the biometric data received from the sensors to predefined levels of biometric data associated with the user;

determining, by the computer, a comfort score of the garment for the user based on the biometric data, the determining further comprising:

receiving, by a long short term memory network in communication with the computer, a particle defined as the garment being worn by the user and at least one feature of the garment as feature vectors of the garment;

measuring, by the long short term memory network, a quality of each particle in multiple intervals of time by: normalizing feature vectors; converging the feature vectors; applying sigmoid functions to the convergence of the feature vectors; applying memory weights to the convergence of the feature vectors; updating the memory weights to store a state of the particle at an interval of time; and outputting a measure of comfort of the garment relative to the user as a comfort score to the computer;

comparing, by the computer, the comfort score of the garment to previously stored comfort scores; and if the comfort score is not acceptable for the garment currently being worn by the user, sending, by the computer, a signal to the conductive threads of the garment while being worn by the user to alter a feature of the garment selected from the group consisting of: texture, shape and size.

16. The computer system of claim 15, wherein, if the comfort score is acceptable, storing the comfort score of the garment associated with the user in a repository.

17. The computer system of claim 15, wherein the garment is worn next to the skin of the user.

18. The computer system of claim 15, further comprising the program instructions of receiving, by the computer, the biometric data of the user from a mobile device.

19. The computer system of claim 15, wherein the conductive threads are made of shape memory materials and alter the shape based on stimuli.

20. The computer system of claim 15, wherein the long short term memory network comprises the computer.

* * * * *